United States Patent [19]

Cosmo et al.

[11] Patent Number: 5,910,605
[45] Date of Patent: Jun. 8, 1999

[54] PROCESS FOR THE PREPARATION OF 3-HYDROXY-2-METHYLBENZOIC ACID AND 3-ACETOXY-2-METHYLBENZOIC

[75] Inventors: Robert Cosmo, Darmstadt; Andreas Dierdorf, Frankfurt, both of Germany

[73] Assignee: Clariant GmbH, Frankfurt, Germany

[21] Appl. No.: 09/019,864

[22] Filed: Feb. 6, 1998

[30] Foreign Application Priority Data

Feb. 11, 1997 [DE] Germany .................. 197 04 885

[51] Int. Cl.[6] .................................................. C07C 65/00
[52] U.S. Cl. ..................... 562/473; 568/647; 260/665 G
[58] Field of Search ........................... 562/473; 568/647; 260/665 G

[56] References Cited

FOREIGN PATENT DOCUMENTS 1028599   5/1966   United Kingdom .

OTHER PUBLICATIONS

Noelting et al., Chem. Berichte, 37, 1015, (1904).

*Primary Examiner*—Paul J. Killos
*Attorney, Agent, or Firm*—Scott E. Hanf

[57] ABSTRACT

The invention relates to a process for the preparation of 3-hydroxy-2-methylbenzoic acid and 3-acetoxy-2-methylbenzoic acid, which comprises reacting 3-chloro-2-methylphenol (3) with benzyl chloride to give 2-benzyloxy-6-chlorotoluene (4) subjecting this to a Grignard reaction with magnesium to give (3-benzyloxy-2-methylphenyl) magnesium chloride (5) reacting this with $CO_2$ to give 3-benzyloxy-2-methylbenzoic acid (6) hydrogenating this or its alkali metal salts in the presence of a hydrogenation catalyst to give 3-hydroxy-2-methylbenzoic acid (2) and optionally acetylating this to give 3-acetoxy-2-methylbenzoic acid.

14 Claims, No Drawings

PROCESS FOR THE PREPARATION OF 3-HYDROXY-2-METHYLBENZOIC ACID AND 3-ACETOXY-2-METHYLBENZOIC

The invention relates to a process for the preparation of 3-hydroxy-2-methylbenzoic acid and 3-acetoxy-2-methylbenzoic acid.

3-Acetoxy-2-methylbenzoic acid (1) is a precursor for HIV protease inhibitors, which are described in U.S. Pat. No. 5,484,926.

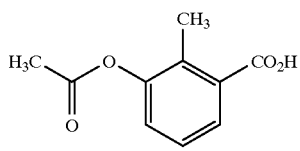

1

3-Acetoxy-2-methlbenzoic acid is prepared from 3-hydroxy-2-methylbenzoic acid (2) using acetic anhydride in the presence of a mineral acid (U.S. Pat. No. 5,484,926, column 111,Example 81).

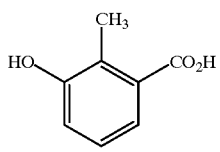

2

The compound 3-hydroxy-2-methylbenzoic acid itself is a key compound for a number of other HIV protease inhibitors. Some of these active compounds are described in WO 95/21164, WO 95/32185 and WO 96/22287.

Numerous syntheses of 3-hydroxy-2-methylbenzoic acid have previously been reported. All prior syntheses of 3-hydroxy-2-methylbenzoic acid, however, have considerable economic and technological disadvantages. According to DRP 91,201, 3-hydroxy-2-methylbenzoic acid is prepared by the fusion of 1,3,5-naphthalenetrisulfonic acid with a very large excess of 50% strength sodium hydroxide solution in an autoclave at 260° C. and subsequent acidic work-up. Napthalene derivatives in which one or two of the sulfo groups of 1,3,5-napthalenetrisulfonic acid are replaced by OH or $NH_2$ can also be employed in this reaction. The very low yields in this process are particularly disadvantageous: for example, only an 18–27% yield of 3-hydroxy-2-methylbenzoic acid is isolated from the disodium salt of 2-naphthylamine-4,8-disulfonic acid [Fieser et al. J. Am. Chem. Soc., 58, 749 (1936)]. Additional disadvantages of this process are the drastic reaction conditions and the high yield of environmentally polluting salt-containing waste water.

A further process starts from 3-chloro-2-methylphenol (Cresp et al., J. Chem. Soc. Perkin Trans.1, 2435(1974)). This is reacted with copper(I) cyanide in pyridine at boiling heat to give 3-hydroxy-2-methylbenzonitrile. In the second stage, the nitrile is hydrolyzed to 3-hydroxy-2-methylbenzoic acid (2) in 18 hours in a boiling mixture of water, glacial acetic acid and concentrated sulfuric acid. The first stage of this process has the significant disadvantage that very toxic copper(I) cyanide is employed—under the reaction conditions toxic hydrogen cyanide gas can escape from the reaction mixture. Harmful pyridine is employed as a solvent. The reaction is distinguished by difficult working up and a high yield of toxic salts. In the second stage (amide hydrolysis), a very long reaction time is necessary. At the very high reaction temperatures, the acidic reaction medium is very corrosive to the materials customarily employed in chemical plants.

Moreau et al., Bull. Soc. Chim. Fr., 3427 (1973), describe the preparation of 3-hydroxy-2-methylbenzoic acid starting from 2-methyl-3-nitrobenzoic acid. 2-Methyl-3-nitrobenzoic acid is reduced to 3-amino-2-methylbenzoic acid by catalytic reduction over palladium/carbon. After diazotization of this amino acid derivative and boiling of the diazonium salt, 3-hydroxy-2-methylbenzoic acid is obtained.

The disadvantage of this synthesis route is the poor availability of the starting substance 2-methyl-3-nitrobenzoic acid. In Kulic et al., J. Gen. Chem. USSR (Engl.), 60, 2118 (1990), the oxidation of 2,3-dimethylnitrobenzene to 2-methyl-3-nitrobenzoic acid is carried out using aqueous potassium permanganate in the presence of a phase-transfer catalyst at 75° C. In this process, 2-methyl-3-nitrobenzoic acid is not obtained as a pure product, but as a mixture with 3-nitrophthalic acid and smaller amounts of 3-methyl-2-nitrobenzoic acid. A complicated purification is necessary in order to obtain pure 2-methyl-3-nitrobenzoic acid from the crude product. This is at the expense of the yield. A further serious disadvantage is the extremely poor space yield of the oxidation reaction. Per 100 ml of water, only 2.4 g of 2,3-dimethylnitrobenzene are employed (see p. 2121). Moreover, manganese dioxide, which has to be disposed of, is formed during the permanganate oxidation.

The oxidation of 2,3-dimethyinitrobenzene using other oxidants also proceeds unsatisfactorily. For example, the oxidation of 2,3-dimethylnitrobenzene using aqueous nitric acid produces the desired 2-methyl-3-nitrobenzoic acid in only 46.6% yield (U.S. Pat. No. 4,065,477, column 4).

An alternative preparation of 2-methyl-3-nitrobenzoic acid comprises the nitration of o-toluic acid (Giacolone, Gazz. Chem. Ital., 65, 840 (1935)). In this nitration, however, the isomeric 2-methyl-5-nitrobenzoic acid is obtained as the main product. Per part of 2-methyl-3-nitrobenzoic acid, 2 parts of 2-methyl-5-nitrobenzoic acid are formed. On the basis of the poor selectivity of the nitration to 2-methyl-3-nitrobenzoic acid, this synthesis is not suitable to make 2-methyl-3-nitrobenzoic acid available in a cost-efficient manner.

A further synthesis of 3-hydroxy-2-methylbenzoic acid (2) starts from 3-methoxybenzoyl chloride. 3-Methoxybenzoyl chloride is reacted with aniline to give 3-methoxy-N-phenylbenzamide. Reaction of 3-methoxy-N-phenylbenzamide with 2 equivalents of n-butyllithium and subsequent alkylation with methyl iodide yields 3-methoxy-2-methyl-N-phenylbenzamide. The reaction of 3-methoxy-2-methyl-N-phenylbenzamide with aqueous hydrochloric acid and aqueous hydrobromic acid in boiling acetic acid leads to the hydrolysis of the amide function and to the cleavage of the methoxy group and to the formation of 3-hydroxy-2-methylbenzoic acid. A disadvantage of the reaction sequence is that very low temperatures (−15° to −70°) are needed in the second stage. Such temperatures can only be realized with difficulty when carrying out the reaction on an industrial scale. In the third stage, very aggressive reaction conditions are necessary to bring about the cleavage of the methoxy group. Moreover, the gaseous substances methyl chloride and methyl bromide, which are suspected of being carcinogenic, are formed as inevitable by-products of the cleavage. Additionally, the acidic reaction medium has a very corrosive action on the materials customarily employed in chemical plants.

There is thus a great need for a process which allows 3-hydroxy-2-methylbenzoic acid and 3-acetoxy-2-methylbenzoic acid to be obtained in an economical and technically simple manner.

This object is achieved by a process for the preparation of 3-hydroxy-2-methylbenzoic acid and 3-acetoxy-2-methylbenzoic acid, which comprises reacting 3-chloro-2-methylphenol (3)

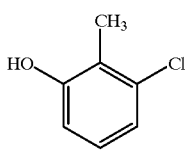

3 with benzyl chloride to give 2-benzyloxy-6-chlorotoluene (4)

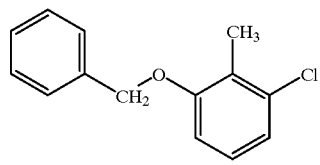

4 subjecting this to a Grignard reaction with magnesium to give (3-benzyloxy-2-methylphenyl)magnesium chloride (5)

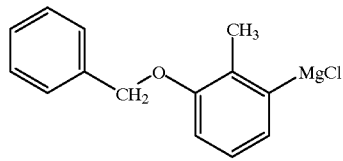

5 reacting this with $CO_2$ to give 3-benzyloxy-2-methylbenzoic acid (6)

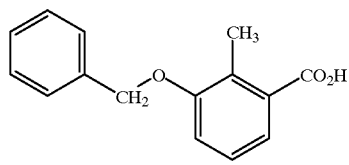

6 hydrogenating this or its alkali metal salts in the presence of a hydrogenation catalyst to give 3-hydroxy-2-methylbenzoic acid (2) and optionally acetylating this to give 3-acetoxy-2-methylbenzoic acid.

The invention likewise relates to the intermediates 2-benzyloxy- 6-chlorotoluene (4), (3-benzyloxy-2-methylphenyl)magnesium chloride (5) and 3-benzyloxy-2-methylbenzoic acid (6).

The process has the significant advantages that it is cost-effective and that the formation of waste products is comparatively low. 3-Chloro-2-methylphenol can be prepared in high yield from the inexpensive starting substance 3-chloro-2-methylaniline by diazotization and subsequent boiling. A process of this type is described in Noelting et al., Chem. Berichte, 37, 1015, (1904).

The alkylation of 3-chloro-2-methylphenol to 2-benzyloxy-6-chlorotoluene can be carried out in a number of solvents, e.g. acetone, methyl ethyl ketone, dimethylformamide. The use of methyl ethyl ketone has proven particularly suitable. Per mole of 3-chloro-2-methylphenol, 1.0 to 5.0 mol, preferably 1.1 to 1.2 mol of benzyl chloride are expediently employed. The alkylation reaction is advantageously carried out in the presence of at least one mol of base such as sodium hydroxide or potassium carbonate per mole of 3-chloro-2-methylphenol. The use of potassium carbonate is convenient. Per mole of 3-chloro-2-methylphenol, 1.0 to 5.0 mol, preferably 2.0 to 2.5 mol, of potassium carbonate are advantageously employed. The product-containing organic solution is filtered from potassium carbonate and worked up by distillation.

The Grignard reaction of 2-benzyloxy-6-chlorotoluene with magnesium to give (3-benzyloxy-2-methylphenyl) magnesium chloride is carried out according to customary methods (see Ullmann's Encyclopedia of Industrial Chemistry, 5th edition, Volume A15, pages 625–626). It has proven suitable to carry out the Grignard reaction in tetrahydrofuran (THF) as the reaction medium.

The reaction of (3-benzyloxy-2-methylphenyl) magnesium chloride with carbon dioxide to give 3-benzyloxy-2-methylbenzoic acid can be carried out such that excess carbon dioxide gas is passed into the solution of the Grignard reagent (5) in THF. The alternative exists of initially introducing THF while passing in carbon dioxide gas and adding the Grignard solution. In this case, a suspension of the magnesium chloride salt of the acid (6) is formed first. The salt is hydrolyzed with sufficient aqueous mineral acid, preferably aqueous hydrochloric acid, such that the free acid (6) is completely liberated.

After the hydrolysis, the product-containing THF phase is separated off from the salt-containing aqueous phase. The isolation of the acid from the solution can be carried out in various ways.

In the carboxylation of the Grignard reagent (5), various other process variants are possible. The carbon dioxide can also be employed in solid form. In this case, it is possible to introduce dry ice into the Grignard solution in portions or to initially introduce the dry ice in the reaction medium and to add the solution of the Grignard reagent. Carbon dioxide can also be employed in liquid form (see, for example, BP 1,028,599).

The hydrogenolysis of 3-benzyloxy-2-methylbenzoic acid to 3-hydroxy2-methylbenzoic acid and toluene is preferably carried out in aqueous medium. In order to improve the solubility of 3-benzyloxy-2-methylbenzoic acid in water, it is advantageous here to add to the reaction mixture at least 1.0 mol of a strong base such as sodium hydroxide or potassium hydroxide (preferably sodium hydroxide) per mole of 3-benzyloxy-2-methylbenzoic acid such that the more water-soluble alkali metal salt of the carboxylic acid is formed. The base can either be added as a solid or as an aqueous solution. The reaction, however, can also be carried out in organic media under neutral conditions. The hydrogenolysis proceeds even at room temperature and at moderate hydrogen pressure (1–10 bar). On the procedure in aqueous basic medium, the catalyst is filtered off after hydrogenolysis is complete. The product-containing aqueous phase is separated from the toluene phase and acidified. The precipitated 3-hydroxy-2-methylbenzoic acid is isolated by filtration.

The customary hydrogenation catalysts such as, for example, palladium on active carbon, platinum on active carbon or Raney nickel can be employed in the hydrogenolysis. The use of palladium on active carbon has proven suitable. Carrying out of the hydrogenolysis in aqueous medium opens up the advantageous possibility of carrying out the catalytic reduction of 3-benzyloxy-2-methylbenzoic acid to 3-hydroxy-2-methylbenzoic acid and the acetylation to give 3-acetoxy-2methylbenzoic acid without intermediate isolation of the hydroxy acid (2).

The hydrogenolysis is in this case expediently carried out in the presence of at least 1.0 mol of the strong base (preferably 2.0 to 3.0 mol) per mole of 3-benzyloxy-2-methylbenzoic acid. Sodium hydroxide is preferably employed as a base. After filtering off the catalyst and separating off the organic toluene phase, the product-containing aqueous phase is treated with acetic anhydride in order to bring about the acetylation. It is advantageous here to employ 1.0 to 3.0 mol of acetic anhydride, preferably 1.2 to 1.6 mol, per mole of 3-benzyloxy-2-methylbenzoic acid employed. The aqueous procedure makes possible a very simple work-up and product isolation: after the acidification of the reaction mixture with a strong mineral acid such as hydrochloric acid, 3-acetoxy-2-methylbenzoic acid is deposited from water as a precipitate which is isolated in high yield by filtration. However, it is also possible to separate off the toluene phase only after the reaction with acetic anhydride.

EXAMPLES

2-Benzyloxy-6-chlorotoluene

A mixture of 143 g (1.0 mol) of 3-chloro-2-methylphenol, 139 g (1.1 mol) of benzyl chloride, 276 g (2.0 mol) of potassium carbonate and 680 g of methyl ethyl ketone (MEK) is heated under reflux with stirring. After 8 hours, a further 25 g (0.18 mol) of potassium carbonate are added and the mixture is then heated under reflux for a further 8 hours. The batch is filtered and the filter cake is washed with MEK. After working up by distillation, 206 g of 2-benzyloxy-6-chlorotoluene (b.p. 161 ° C., 3 mbar) are obtained as a pale yellow liquid in 99.6% purity (surface area % according to GC). This corresponds to a yield of 88.3% of theory.
$^1$H NMR (CDCl$_3$, 60 MHz):δ(ppm): 6.6–7.4 (m, 8H); 5.0 (s, 2H); 2.3 (s, 3H).
GC-MS: M$^+$=232

3-Benzyloxy-2-methylbenzoic acid 232.7 g of 2-benzyloxy-6-chlorotoluene (232.7 g, 1.0 mol) are subjected to a Grignard reaction with 26.7 g (1.1 mol) of magnesium turnings in 550 ml of THF. The brown-black solution of (3-benzyloxy-2-methylphenyl)magnesium chloride in THF formed therefrom is stirred until cold by means of an ice bath at 0° C. CO$_2$ gas is passed into the stirred reaction mixture slowly such that the temperature does not exceed 10° C. The solid suspension in THF formed therefrom is hydrolyzed with cooling by slow addition of 50 ml of water and 445 g (1.2 mol) of hydrochloric acid (10% strength). The hydrolyzed reaction mixture is diluted with 430 g of xylene. The phases are separated and the organic phase is washed with 100 g of water. The product-containing organic phase separated off is distilled until the bottom is free of THF. The bottom is then stirred at 0° C. until cold. The crystallized product is filtered off and washed with 50 ml of xylene. After drying in vacuo, 152.3 g of 3-benzyloxy-2-methylbenzoic acid are obtained. This corresponds to a yield of 62.9% of theory.
Melting point: 126–127° C.

$^1$H NMR (DMSO-d$_6$, 60 MHz): δ(ppm): 12.9 (bs, 1H); 7.6–7.1 (m, 8H); 5.1 (s, 2H); 2.4 (s, 3H).
GC-MS: M$^+$=242

3-Hydroxy-2-methylbenzoic acid

A solution of 3-benzyloxy-2-methylbenzoic acid (50 g, 0.21 mol) and sodium hydroxide (9 g, 0.225 mol) in 700 g of water and 2 g of 5% Pd/C catalyst (50% water-moist) are added to a 2l steel autoclave with an aerating stirrer. 10 bar of hydrogen are injected at a temperature of 50° C. and a stirring speed of 800 rpm. Consumed hydrogen is replaced by repeated injection. After 20 min, the absorption of hydrogen falls off. The catalyst is filtered off at room temperature by means of a pressure filter. 760.7 g of a crude solution are obtained, from which 7.7 g of toluene are separated off in a separating funnel. A total of 22.2 g of hydrochloric acid (37% strength) are added to the crude solution, then the solution is cooled to 0° C. The precipitated solid is filtered off with suction and washed twice with 50 g of water. After drying, 18.0 g of 3-hydroxy-2-methylbenzoic acid having a melting point of 147° C. are obtained. After concentration of the mother liquor, a further 9.6 g of substance can be obtained, such that the total yield is 27.6 g or 88.1% of theory.

3-Acetoxy-2-methylbenzoic acid 60.9 g (0.40 mol) of 3-hydroxy-2-methylbenzoic acid are introduced into 500 ml of 2N sodium hydroxide solution (1.00 mol) with stirring and the solution formed in the course of this is cooled to 5° C. 61.3 g (0.60 mol) of acetic anhydride are added to the cooled solution. The reaction mixture is cooled here such that the temperature does not exceed 8° C. The reaction mixture is then acidified with 88 ml of 37% hydrochloric acid. The precipitated product is filtered off, washed three times with 50 ml of water and dried in vacuo. 69.9 g of 3-acetoxy-2-methylbenzoic acid are obtained. This corresponds to a yield of 90.0% of theory. Melting point 147–148° C.

3-Acetoxy-2-methylbenzoic acid by hydrogenolysis of 3-benzyloxy-2-methylbenzoic acid and subsequent acetylation without intermediate isolation of 3-hydroxy-2-methylbenzoic acid.

A solution of 3-benzyloxy-2-methylbenzoic acid (50 g, 0.21 mol) and sodium hydroxide (20 g, 0.5 mol) in 700 g of water and 2 g of 5% Pd/C catalyst (50% water-moist) is added to a 2l steel autoclave with an aerating stirrer. 10 bar of hydrogen are injected at a temperature of 25° C. and a stirring speed of 800 rpm. Consumed hydrogen is replaced by repeated injection. After 15 min, the absorption of hydrogen falls off. The catalyst is filtered off at room temperature through a pressure filter. 735.8 g of a crude solution are obtained, from which 7.1g of toluene are separated off in a separating funnel. The aqueous crude solution is cooled to 0° C. in a 1 l four-necked flask with a pH meter. The pH is 14. 31.3 g (0.3 mol) of acetic anhydride are added dropwise in the course of 5 min; the pH falls to 6.0. The solution is then slowly treated (pH 1.1) with 49.3 g (0.5 mol) of hydrochloric acid (37% strength). A white precipitate is deposited in the course of this. The suspension is stirred for a further half hour, then the precipitate is filtered off and washed twice with 50 g of ice water. After drying, 37.5 g (93.7% of theory) of 3-acetoxy-2-methylbenzoic acid are obtained (melting point: 147° C.).

We claim:
1. A process for the preparation of 3-hydroxy-2-methylbenzoic acid and 3-acetoxy-2-methylbenzoic acid, which comprises reacting 3-chloro-2-methylphenol (3)

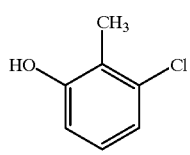

3 with benzyl chloride to give 2-benzyloxy-6-chlorotoluene (4)

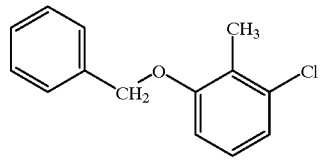

4 subjecting this to a Grignard reaction with magnesium to give (3-benzyloxy-2-methylphenyl)magnesium chloride (5)

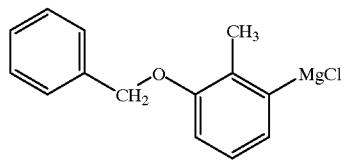

5 reacting this with $CO_2$ to give 3-benzyloxy-2-methylbenzoic acid (6)

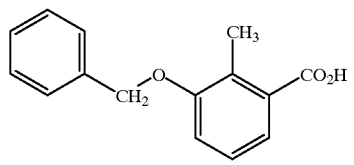

6 hydrogenating this or its alkali metal salts in the presence of a hydrogenation catalyst to give 3-hydroxy-2-methylbenzoic acid (2) and optionally acetylating this to give 3-acetoxy-2-methylbenzoic acid.

2. The process as claimed in claim 1, wherein methyl ethyl ketone is employed as a reaction medium in the benzylation of 3-chloro-2-methylphenol (3) to 2-benzyloxy-6-chlorotoluene (4).

3. The process as claimed in claim 1, wherein per mole of 3-chloro-2-methylphenol (3) 1.0 to 5.0 mol of benzyl chloride and 1.0 to 5.0 mol of potassium carbonate are employed in the benzylation of 3-chloro-2-methylphenol (3) to 2-benzyloxy-6-chlorotoluene (4).

4. The process as claimed in claim 1, wherein per mole of 3-chloro-2methylphenol (3) 1.1 to 1.2 mol of benzyl chloride and 2.0 to 2.5 mol of potassium carbonate are employed in the benzylation of 3-chloro-2-methylphenol (3) to 2-benzyloxy-6-chlorotoluene (4).

5. The process as claimed in claim 1, wherein the reaction of 2-benzyloxy-6-chlorotoluene (4) with magnesium to give (3-benzyloxy-2-methylphenyl)magnesium chloride (5) is carried out in tetrahydrofuran as reaction medium.

6. The process as claimed in claim 1, wherein the hydrogenation catalyst is palladium on active carbon.

7. The process as claimed in claim 1, wherein the hydrogenation of the sodium salt of 3-benzyloxy-2-methylbenzoic acid (6) to 3-hydroxy-2-methylbenzoic acid (2) and toluene is carried out in aqueous medium.

8. The process as claimed in claim 1, wherein the 3-benzyloxy-2-methylbenzoic acid (6) obtained as claimed in claim 1 is hydrolyzed to 3-hydroxy-2-methylbenzoic acid (2) and toluene in the basic aqueous medium in the presence of a hydrogenation catalyst, the catalyst is separated off by filtration, the aqueous phase is separated off from the toluene phase and reacted with acetic anhydride, and the reaction mixture is acidified.

9. A compound of 2-Benzyloxy-6-chlorotoluene (4) having the formula:

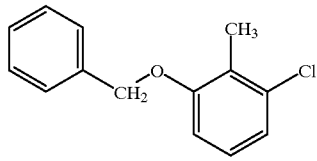

4

10. A compound of (3-Benzyloxy-2-methylphenyl) magnesium chloride (5) having the formula:

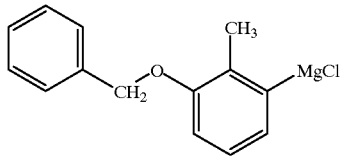

5

11. A compound of 3-Benzyloxy-2-methylbenzoic acid (6) having the formula:

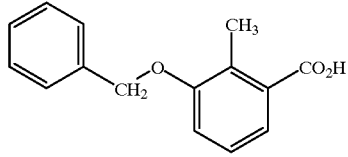

6

12. A compound of 2-Benzyloxy-6-chlorotoluene (4) having the formula:

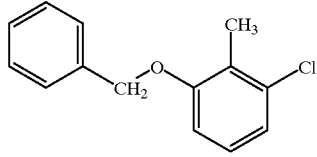

4 produced by the process of claim 1.

13. A compound of (3-Benzyloxy-2-methylphenyl) magnesium chloride (5) having the formula:

produced by the process of claim 1.
14. A compound of 3-Benzyloxy-2-methylbenzoic acid (6) having the formula:
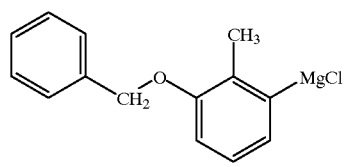
produced by the process of claim 1.
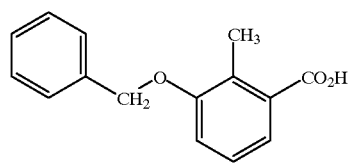
* * * * *